United States Patent
Vu et al.

(10) Patent No.: US 12,251,210 B2
(45) Date of Patent: Mar. 18, 2025

(54) RESPIRATION RATE MEASUREMENT SYSTEM

(71) Applicant: The Regents of the University of Colorado, Denver, CO (US)

(72) Inventors: Tam Ngoc Vu, Boulder, CO (US); Robin Deterding, Boulder, CO (US); Hoang Truong, Boulder, CO (US); Nam Ngoc Bui, Broomfield, CO (US)

(73) Assignee: The Regents of the University of Colorado, Denver, CO (US)

( * ) Notice: Subject to any disclaimer, the term of this patent is extended or adjusted under 35 U.S.C. 154(b) by 802 days.

(21) Appl. No.: 17/284,066

(22) PCT Filed: Oct. 9, 2019

(86) PCT No.: PCT/US2019/055467
§ 371 (c)(1),
(2) Date: Apr. 9, 2021

(87) PCT Pub. No.: WO2020/077002
PCT Pub. Date: Apr. 16, 2020

(65) Prior Publication Data
US 2021/0401322 A1    Dec. 30, 2021

Related U.S. Application Data

(60) Provisional application No. 62/744,062, filed on Oct. 10, 2018.

(51) Int. Cl.
*A61B 5/08*     (2006.01)
*A61B 5/00*     (2006.01)
(Continued)

(52) U.S. Cl.
CPC .......... *A61B 5/0816* (2013.01); *A61B 5/0004* (2013.01); *A61B 5/0878* (2013.01);
(Continued)

(58) Field of Classification Search
CPC ... A61B 5/0816; A61B 5/0878; A61B 5/7246; A61B 2562/0204; A61B 2562/0247; A61B 2562/0271; A61B 5/087
See application file for complete search history.

(56) References Cited

U.S. PATENT DOCUMENTS

2011/0071406 A1* 3/2011 Addison ............. A61B 5/0205
                                                        600/529
2015/0112605 A1* 4/2015 Watson .................... A61B 5/08
                                                          702/19

(Continued)

FOREIGN PATENT DOCUMENTS

JP        2018098542 A    6/2018
TW         201236229 A    9/2012
WO    WO 2017/036500 A1   3/2017

OTHER PUBLICATIONS

Holtzman, M., Arcelus, A., Goubran, R., & Knoefel, F. (2008). Breathing signal fusion in pressure sensor arrays. 2008 IEEE International Workshop on Medical Measurements and Applications, 71-76. https://doi.org/10.1109/memea.2008.4543001 (Year: 2008).*

(Continued)

*Primary Examiner* — May A Abouelela
*Assistant Examiner* — Samuel C Kim
(74) *Attorney, Agent, or Firm* — Craig R. Miles; CR MILES P.C.

(57) ABSTRACT

A respiration rate measurement apparatus including a plurality of sensors for concurrently generating temperature, pressure and acoustic data representing one or more successive breaths and a method of generating fusion data from the plurality of data streams as a weighted average based on determined correlation coefficients and calculation of a respiratory rate.

15 Claims, 16 Drawing Sheets

(51) Int. Cl.
  *A61B 5/087* (2006.01)
  *G16H 40/67* (2018.01)
  *G16H 50/70* (2018.01)
  *G16H 50/20* (2018.01)

(52) U.S. Cl.
  CPC .......... *A61B 5/6898* (2013.01); *A61B 5/7246* (2013.01); *A61B 5/7278* (2013.01); *A61B 5/7435* (2013.01); *A61B 5/7475* (2013.01); *G16H 40/67* (2018.01); *G16H 50/70* (2018.01); *A61B 5/0803* (2013.01); *A61B 2562/0204* (2013.01); *A61B 2562/0247* (2013.01); *A61B 2562/0271* (2013.01); *G16H 50/20* (2018.01)

(56) References Cited

U.S. PATENT DOCUMENTS

| | | | |
|---|---|---|---|
| 2016/0051162 A1* | 2/2016 | Durand | A61B 5/377 600/544 |
| 2016/0051205 A1* | 2/2016 | Al-Ali | A61B 5/02416 600/301 |
| 2016/0150981 A1* | 6/2016 | Baker | A61B 5/0878 600/479 |
| 2016/0151603 A1 | 6/2016 | Shouldice et al. | |
| 2017/0188864 A1 | 7/2017 | Drury | |
| 2017/0249434 A1 | 8/2017 | Brunner | |
| 2017/0319129 A1 | 11/2017 | Shah et al. | |

OTHER PUBLICATIONS

Bakr, M. A., & Lee, S. (2017). Distributed multisensor data fusion under unknown correlation and data inconsistency. Sensors, 17(11), 2472. https://doi.org/10.3390/s17112472 (Year: 2017).*

PCT International Patent Application No. PCT/US19/55467, International Search Report and Written Opinion of the International Searching Authority dated Jan. 2, 2020, 12 pages.

* cited by examiner

RESPIRATION RATE MEASUREMENT SYSTEM

This application is the United States National Stage of International Patent Cooperation Treaty Patent Application No. PCT/US19/55467, filed Oct. 9, 2019, which claims the benefit of U.S. Provisional Patent Application No. 62/744,062, filed Oct. 10, 2018, each hereby incorporated by reference herein.

I. TECHNICAL FIELD

A respiration rate measurement apparatus including a plurality of sensors which concurrently generate temperature data, pressure data and acoustic data representing one or more successive breaths and a method of generating fusion data from the temperature, pressure and acoustic data streams as a weighted average based on determined correlation coefficients applied to the data streams and calculation of a respiratory rate.

II. DISCLOSURE OF THE INVENTION

A broad object of the invention can be provision of a respiratory rate measurement apparatus including a respiratory air temperature sensor adapted to sense respiratory air temperature in a respiratory air flow, a respiratory air acoustic sensor adapted to sense respiratory air acoustic energy in the respiratory air flow, and a respiratory air pressure sensor adapted to sense respiratory air pressure in the respiratory air flow, each sensor concurrently generating data which varies based on sensed change in a corresponding respiratory air property during exhalation of one or more breaths. A processor unit including a processor communicatively coupled to a non-transitory computer readable memory containing a respiratory rate measurement program (also referred to as the "program") can function to discretely analyze variance in sensor data generated by each sensor to establish a confidence metric in the sensor data from which correlation coefficients can be derived as the normalization of the confidence metric in a range of about 0.1 to about 0.9 which can be utilized to calculate fusion data as a weighted average based on determined correlation coefficients and calculate a respiratory rate.

Another broad object of the invention can be provision of a method of measuring a respiratory rate including: sensing respiratory air temperature in a respiratory airflow with a respiratory air temperature sensor, sensing respiratory air acoustic energy in a respiratory airflow with a respiratory air acoustic energy sensor; and sensing respiratory air pressure in a respiratory airflow with a respiratory air pressure sensor; and generating data which varies based on sensed change in the corresponding respiratory air property during exhalation of one or more breaths. The method can further include: discretely analyzing covariance in each of the respiratory air temperature data, the respiratory air acoustic energy data, and the respiratory air pressure data; determining correlation coefficients based on analyzed covariance in each of the respiratory air temperature data, the respiratory air acoustic energy data, and said respiratory air pressure data; fusing the respiratory air temperature data, the respiratory air acoustic energy data, and the respiratory air pressure data as a weighted average based on the covariance coefficients to generate fusion respiratory rate data; and calculating a respiratory rate based on the fusion respiratory rate data.

Another broad object of the invention can be provision of a method of using a respiratory rate measurement apparatus including disposing a respiratory rate measurement apparatus in a respiratory airflow, the respiratory rate measurement device including: a respiratory air temperature sensor; a respiratory air acoustic sensor; and a respiratory air pressure sensor, each disposed in fixed spatial relation to concurrently sense the respiratory air flow of one or more breaths; and a processor unit communicatively coupled to the respiratory air temperature sensor, the respiratory air acoustic sensor, and the respiratory air pressure sensor, the processor unit configured to fuse the respiratory air temperature data, respiratory air acoustic energy data, and respiratory air pressure data as a weighted average based on analyzed covariance of the sensor data and calculate a respiratory rate.

Naturally, further objects of the invention are disclosed throughout other areas of the specification, drawings, photographs, and claims.

III. BRIEF DESCRIPTION OF THE DRAWINGS

IV. MODE(S) FOR CARRYING OUT THE INVENTION

Figure 1A:
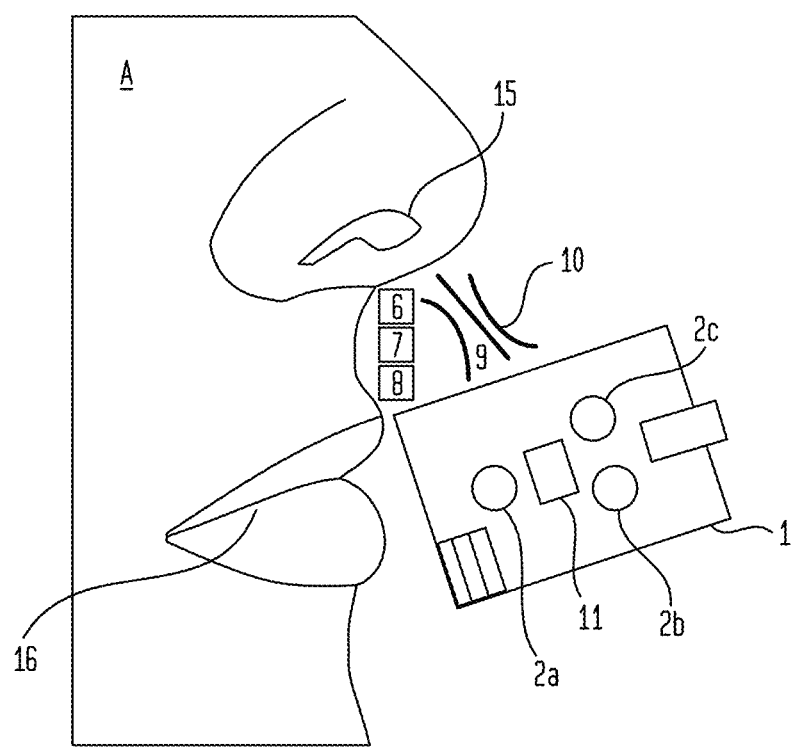
FIG. 1A is an illustration of a method of using an embodiment of the respiration rate measurement apparatus.

Generally, referring to FIGS. 1A through 14, which depict embodiments of a respiration rate measurement apparatus (1) including a plurality of sensors (2)(2A, 2B, 2C . . . ) which concurrently generate temperature data (3), pressure data (4), and acoustic data (5) representing sensed change in the respiratory airflow temperature (6), respiratory airflow pressure (7), and respiratory airflow acoustic energy (8) in a respiratory airflow (9) of one or more breaths (10) and a processor unit (11) communicatively coupled to each of the plurality of sensors (2) which includes a processor (11A) communicatively coupled to a non-transitory computer readable media (11B) containing a respiratory rate measurement program (12) executable to fuse the temperature data (3), the pressure data (4) and acoustic data (5) as a weighted average based on analyzed confidence metrics (21) of the data (3)(4)(5) from each of the plurality of sensors (3), and based on derived correlation coefficients (23) to generate fusion data (13) and calculate a respiratory rate (14).

Again, generally referring to FIGS. 1A through 14, methods of using embodiments of the respiration rate measurement apparatus (1) can include or consist of: disposing a respiratory rate measurement apparatus (1) in a respiratory airflow (9), where the respiratory rate measurement apparatus (1) includes: a respiratory air temperature sensor (2A); a respiratory air acoustic sensor (2B); and a respiratory air pressure sensor (2C), each disposed in fixed spatial relation to concurrently sense the respiratory air flow (9) of one or successive breaths (10) whether through the nostrils (15) (as shown in the illustrative example of FIG. 1A) or through the oral cavity (16) (as shown in the illustrative example of FIG. 1B), or combinations thereof, and a processor unit (11) communicatively coupled to each of the respiratory air temperature sensor (2A), the respiratory air acoustic sensor (2B), and the respiratory air pressure sensor (2C), the processor unit executing a respiratory rate measurement program (12) to fuse the respiratory airflow temperature data (3), respiratory airflow acoustic energy data (4), respiratory airflow pressure data (5) as a weighted average based on analyzed confidence metrics (21) of the data (3)(4)(5) from each of the plurality of sensors (2), and based on the derived correlation coefficients (23) to generate fusion data (13) and calculate a respiratory rate (14).

For the purposes of this invention the term "respiratory airflow" means the flow of air that is exhaled from the nostrils (15) or oral cavity (16) of an animal (A) in the process of breathing (10). An animal (A) can be a human or non-human animal.

Figure 1B:
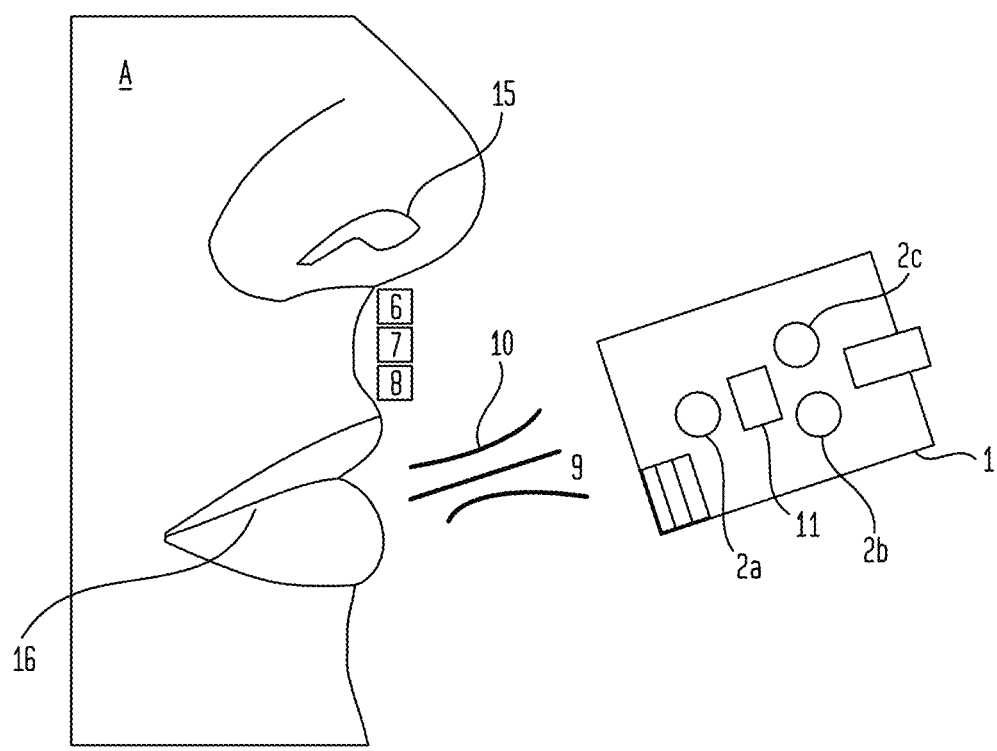
FIG. 1B is an illustration of a method of using an embodiment of the respiration rate measurement apparatus.
Figure 2:
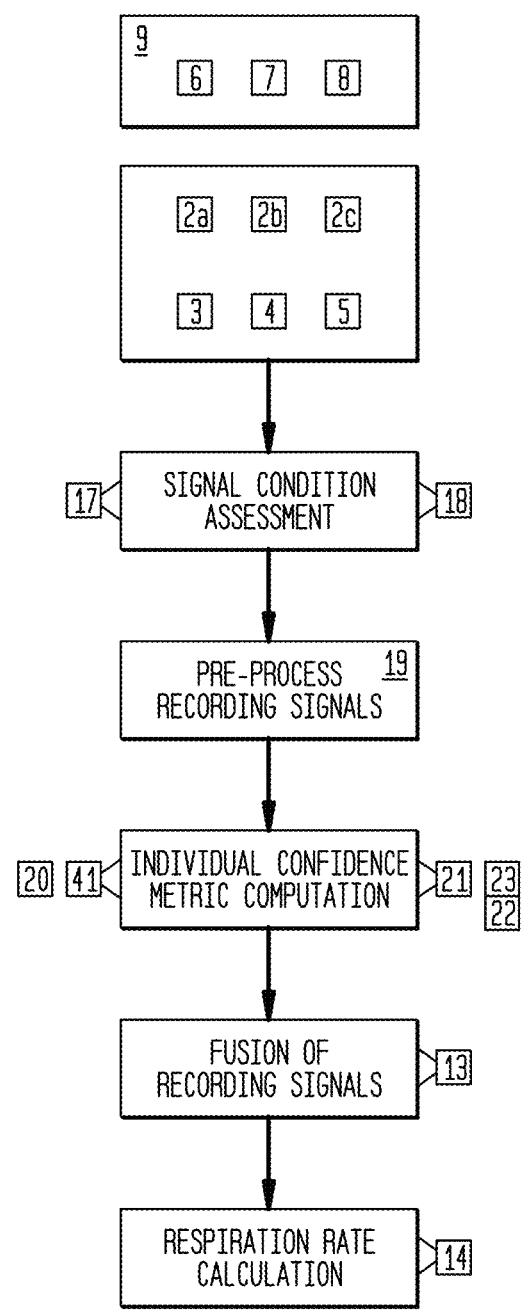
FIG. 2 is a block flow diagram of a method of processing sensor data to obtain a respiration rate calculation.

Now, with primary reference to FIGS. 1A, 1B, and 2, a method in embodiments of a respiration rate measurement apparatus (1) can include: sensing respiratory airflow temperature (6) in a respiratory airflow (9) with a respiratory air temperature sensor (2A) and generating respiratory airflow temperature data (3) varying based on sensed change in the respiratory airflow temperature (6); sensing respiratory airflow pressure (7) in a respiratory airflow (9) with a respiratory air pressure sensor (2C) and generating respiratory airflow pressure data (4) varying based on sensed change in respiratory airflow pressure (7)); sensing respiratory airflow acoustic energy (8) in the respiratory airflow (9) with a respiratory airflow acoustic energy sensor (2C) and generating respiratory airflow acoustic data (5) varying based on sensed change in said respiratory airflow acoustic energy (8). In particular embodiments, sensing respiratory airflow (9) and generating respiratory airflow data (3) (4) or (5) can, but need not necessarily, occur as to one of the plurality of sensors (2A) or (2B) or (2C), or can concurrently occur as to two of the plurality of sensors (2A)(2B)(2C) in various combinations, or can occur concurrently as to all of the plurality of sensors (2A)(2B)(2C).

There can be a substantial advantage in disposing a plurality of sensors (2) (respiratory airflow temperature sensor (2A), respiratory airflow pressure sensor (2B), respiratory airflow acoustic sensor (2C)) in a respiratory airflow (9) and fusion of the data (temperature data (3), pressure data (4) and acoustic data (5)) as a weighted average based on analyzed confidence metrics confidence metrics (21) for each of the respiratory airflow temperature data (3), the respiratory airflow pressure data (4), and the respiratory airflow acoustic energy data (5)) and based on derived correlation coefficients (23) generate the fusion data (13) and calculate a respiratory rate (14). Each of the plurality of sensors (2) can, depending on use or external conditions (or combinations thereof), generate data (3)(4)(5) which to a greater or lesser degree accurately represents the respiratory airflow (9) associated with one or a plurality of successive breaths (10). As illustrative examples, the respiratory airflow temperature sensor (2A) sensing respiratory airflow temperature (6) associated with fast breathing (10) may generate an upwardly trending dielectric constant ("DC trend") associated with the respiratory airflow temperature data (3), while the airflow acoustic energy sensor (2C) sensing respiratory airflow acoustic energy (8) associated with breathing (10) proximate the nostrils (15) may generate acoustic energy data (5) having less noise than when sensing respiratory airflow acoustic energy (8) distal from the nostrils (15), while the respiratory airflow pressure sensor (2B) sensing respiratory airflow pressure (7) associated with breathing (10) proximate the nostrils (15) may generate respiratory airflow pressure data (4) having greater background noise than sensing respiratory airflow pressure (7) associated with breathing (10) distal from the nostrils (15).

Figure 3:
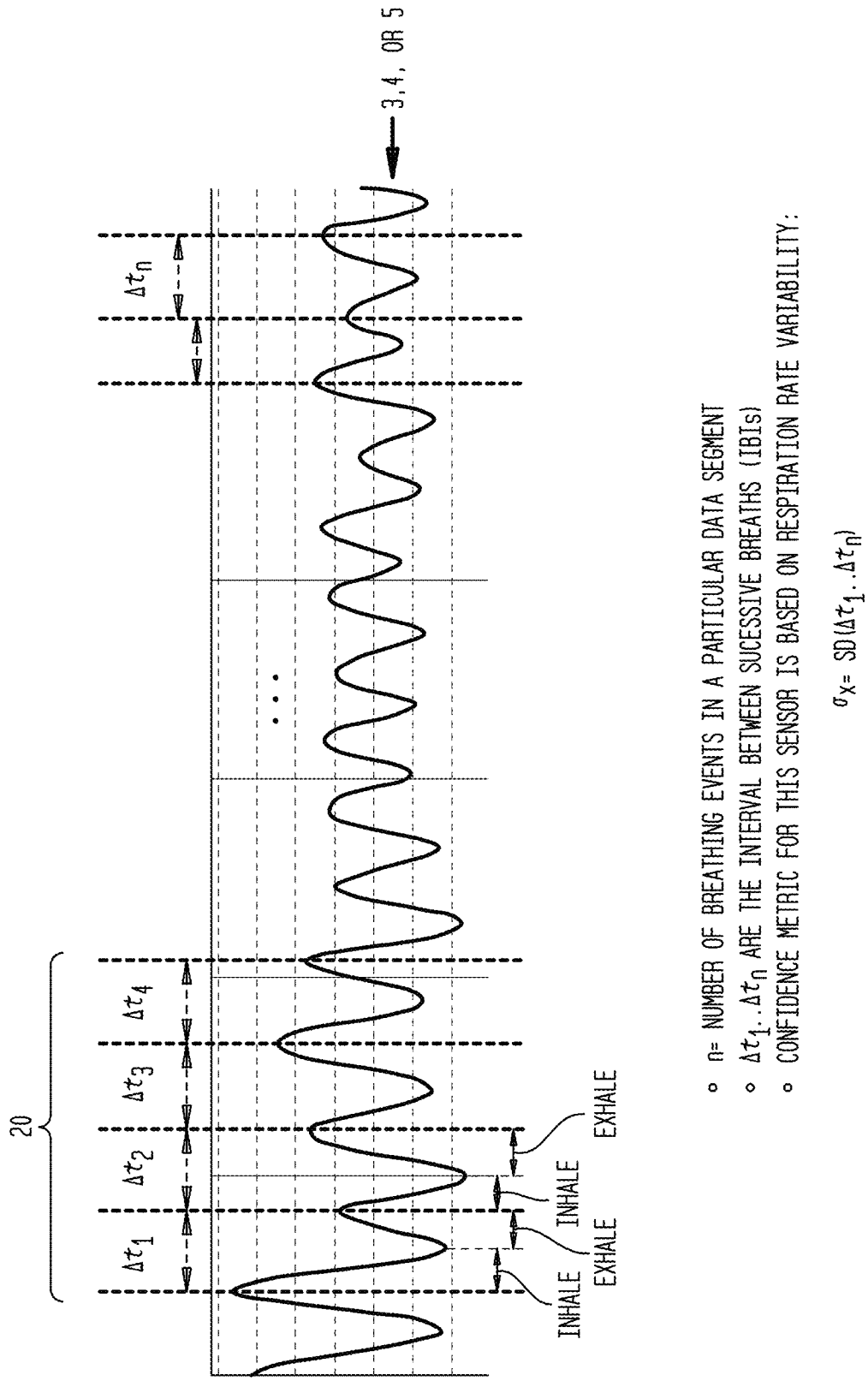
FIG. 3 is an illustration of a method of processing sensor data to determine respiration rate variability and calculation of a confidence metric based on respiration rate variability.

Accordingly, with primary reference to FIGS. 2 and 3, the data (3)(4)(5) recorded from each of the plurality of sensors (2)(2A)(2B)(2C) can be compared with a pre-recording noise level (17) to confirm whether the corresponding data (3)(4)(5) has a signal condition level (18) sufficient for pre-processing (19) (as shown in the example of FIG. 2 as "Signal Condition Assessment"). The data (3)(4)(5) can be further pre-processed (19) to remove the DC trend, to cancel noise or to filter out undesired frequency band(s) (as shown in the example of FIG. 2 as "Pre-process Recording Signals (19)"). Based on respiration rate variability (20) or interval between successive breaths ($\Delta t_1$, $\Delta t_2$, $\Delta t_3$, $\Delta t_4$) (as shown in the example of FIG. 3), a confidence metric (21) can be computed (as shown in the example of FIG. 2 as "Individual Confidence Metric Computation) which can then be utilized to determine correlation coefficients (23) which can be utilized in a covariance matrix (22) which can be correspondingly applied to the each of the respiratory airflow temperature data (3), the respiratory airflow pressure data (4), and the respiratory airflow acoustic energy data (5) to generate fusion data (13) as a weighted average of the data (3)(4)(5) generated by the plurality of sensors (2) (as shown in the example of FIG. 2 as "Fusion of Recording Signals"). A respiratory rate (14) can be calculated from the fusion data (13) (as shown in the example of FIG. 2 as "Respiratory Rate Calculation). The respiratory rate (14) calculated from the fusion data (13) from two or more sensors (2) can have greater precision or accuracy, than if calculated based on the data (3)(4) or (5) from only one sensor (2A)(2B) or (2C).

Figure 4A:
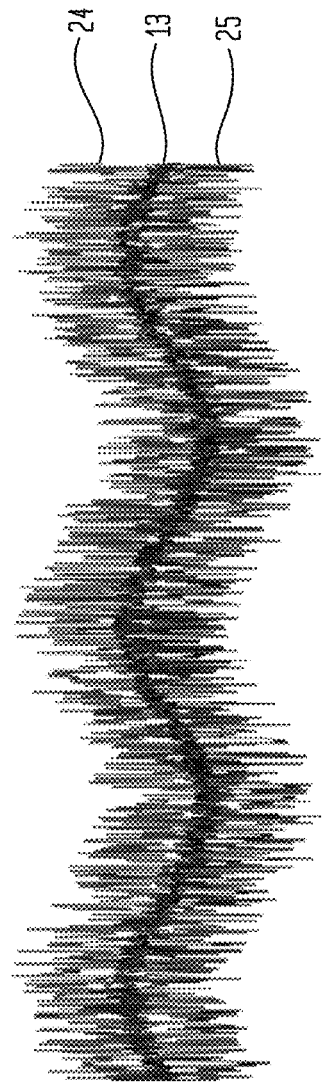
FIG. 4A is an illustration of a result of applying a fusion model to sensor data from a plurality of sensors having substantially the same confidence metrics.
Figure 4B:
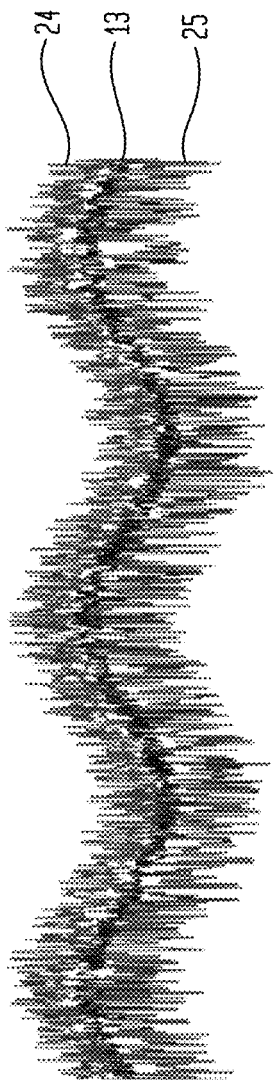
FIG. 4B is an illustration of a result of applying a fusion model to sensor data from a plurality of sensors having substantially different confidence metrics.

Now, with primary reference to FIGS. 4A and 4B, in particular embodiments, the method of generating the fusion data (13) can, but need not necessarily, be accomplished using the Kalman fusion model or similar models. Also known as linear quadratic estimation ("LQE"), an algorithm uses a series of measurements observed over time, containing statistical noise and other inaccuracies, and produces estimates of unknown variables that tend to be more accurate than those based on a single measurement alone, by estimating joint probability distribution over the variables for each timeframe.

As exemplified in the illustrative examples of FIGS. 4A and 4B, with a first sensor data (24) and a second sensor data (25), when each of the first and second sensor data (24)(25) have substantially the same confidence metric (21) then the fusion data (13) comprises an average of the first sensor data (24) and the second sensor data (25) given substantially equal weight (as shown in the example of FIG. 4A); however, when the second sensor data (25) has a greater confidence metric (21) than the first sensor data (24), then the fusion data (13) comprises a weighted average in which the second sensor data (25) is given greater weight than the first sensor data (24) (as shown in the example of FIG. 4B).

In a particular embodiment in one state of respiratory airflow (9) and three observations from each of three sensors (2A)(2B)(2C) it can be predicted that:

$$\hat{x}_k = A\hat{x}_{k-1} = 1 * \hat{x}_{k-1} = \hat{x}_{k-1}$$

$$P_k = AP_{k-1}A = P_{k-1}$$

Which can be updated using LQE to yield:

$$G_k = P_k C^T (CP_k C^T + R)^{-1}$$

Where:

$$C = \begin{bmatrix} 1 \\ 1 \\ 1 \end{bmatrix}, R = \begin{bmatrix} Coeff_1 & 0 & 0 \\ 0 & Coeff_2 & 0 \\ 0 & 0 & Coeff_3 \end{bmatrix}$$

$$\hat{x}_k \leftarrow \hat{x}_k + G_k(z_k - C\hat{x}_k)$$

$$P_k \leftarrow (I - G_k C) P_k$$

Where:
Coeff$_{1\ldots 3}$ are derived from individual sensor confidence metrics (21) as the normalization of those confidence metrics (21) in range of 0.1 to 0.9.

Now, with primary reference to FIG. 5, which depicts an illustrative example of a processing timeline (26) for a particular sensor (2A)(2B) or (2C) which comprises a start time (27) at zero time and a first-time interval (28) which elapses at about two seconds along the processing timeline (26)(although any time interval suitable to collect pre-recording data can be utilized) in which a pre-recording noise level (17) can be collected for later comparative signal condition assessment. The illustrative example of the processing timeline (26) further includes a second-time interval (29) in which a sliding measurement window (30) of y seconds width corresponds to the total number of time points that will be included in a measurement window (31). The sliding measurement window (30) transitions along the processing timeline (26) in x second increments to generate an overlapping set of measurement windows (32), each of which are accorded a confidence metric (21). Every time the data (3)(4) or (5) within a measurement window (31) finishes processing, confidence metrics (21) and correlation coefficients (23) can be updated which correspondingly update the fusion data (13).

Figure 6A:
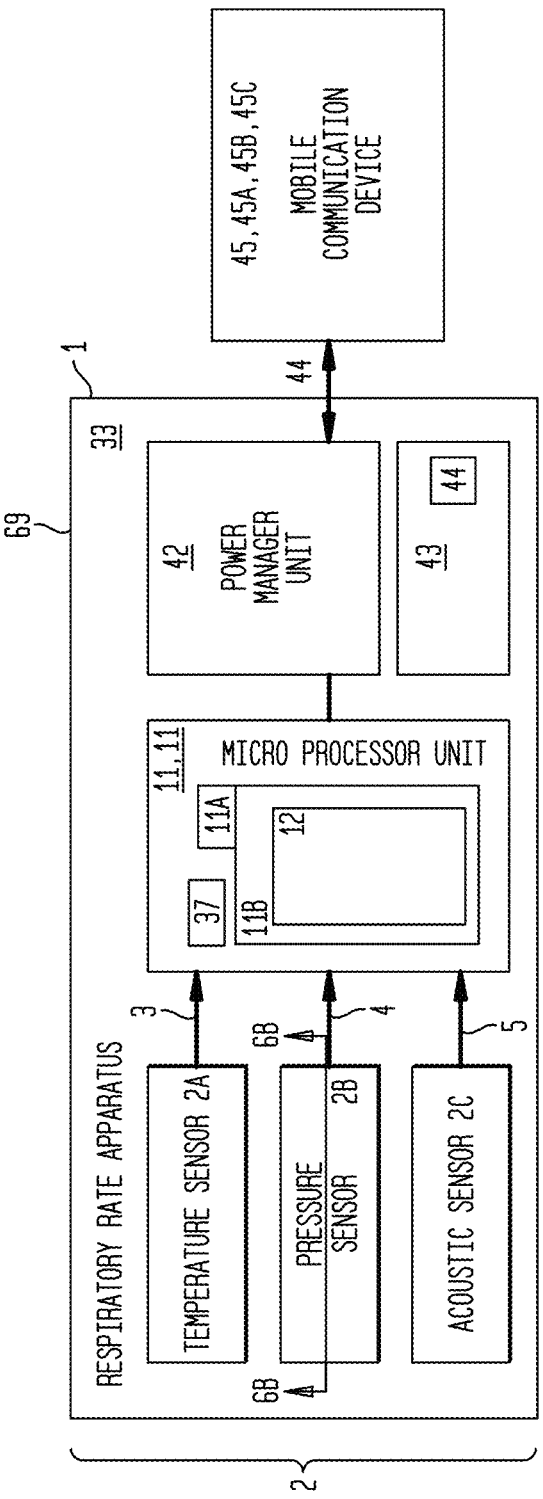
FIG. 6A is a block diagram of an embodiment of the respiration rate measurement apparatus.
Figure 6B:
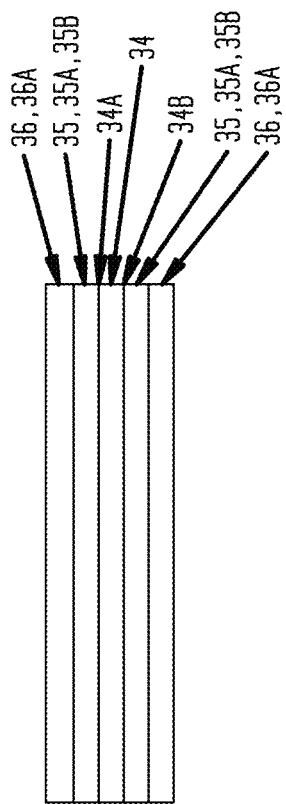
FIG. 6B is a cross section diagram of an embodiment of the respiratory airflow pressure sensor (2B) shown in FIG. 6A.

Now, with primary reference to FIGS. 6A and 6B, embodiments of a respiratory airflow measurement apparatus (1) can include or consist of one or more of: a respiratory airflow temperature sensor (2A) adapted to sense respiratory airflow temperature (6) in a respiratory airflow (9), a respiratory airflow pressure sensor (2B) adapted to sense respiratory airflow pressure (7) in the respiratory air flow (9), a respiratory airflow acoustic sensor (2C) adapted to sense respiratory airflow acoustic energy (8) in the respiratory airflow (9). The respiratory airflow temperature sensor (2A), the respiratory airflow acoustic sensor (2B), and the respiratory airflow pressure sensor (2C) can, but need not necessarily, have a fixed spatial relationship to concurrently sense a respiratory airflow (9) associated with breathing (10) of an animal (A).

As shown in the illustrative example of FIGS. 1A, 1B and 6A, the respiratory airflow temperature sensor (2A), the respiratory airflow acoustic sensor (2B), and the respiratory airflow pressure sensor (2C) be disposed on a printed circuit board (33) in a fixed spatial relation which allows the respiratory airflow (9) associated with breathing (10) through the oral cavity (16) or through the nostrils (15) to concurrently fluidically engage each of the respiratory airflow temperature sensor (2A), the respiratory airflow pressure sensor (2B), and the respiratory airflow acoustic sensor (2C).

Now, with primary reference to FIG. 6A, the respiratory airflow temperature sensor (2A) can generate respiratory airflow temperature data (3) varying based on sensed change in the respiratory airflow temperature (6). In particular embodiments, the respiratory airflow temperature sensor (2A) can comprise or consist of a thermistor adapted to sense respiratory airflow temperature (6) of about 20° C. to about 45° C. As an example, a thermistor suitable for use in embodiments can be a PN: QT0805Z-104F available from Quality Thermistor, Inc. 2108 South Century Way, Boise, ID 83709.

Again, with primary reference to FIGS. 6A and 6B, the respiratory airflow pressure sensor (2B) can generate respiratory airflow pressure data (4) varying based on sensed change in respiratory airflow pressure (7). As shown in the illustrative example of FIG. 6B, the respiratory airflow pressure sensor (2B) can comprise or consist of a piezoelectric film (34) overlaid on one or both piezoelectric film faces (34A)(34B) by an electrically conductive layer (35) and an insulator layer (36). Similar to piezoelectric quartz and ceramic materials, piezoelectric film (34) can produce voltage or charge proportional in both amplitude and frequency to applied dynamic strain. The piezoelectric film (34) can have a thickness of about 20 micrometers to about 200 micrometers. As an example, the piezoelectric film (34) can have a thickness of about 20 micrometers to about 50 micrometers and be more sensitive to vibration but may also be sensitive to acoustic energy (8), or as a further example, the piezoelectric film (34) can have a thickness of about 150 micrometers to about 200 micrometers and can be less sensitive to acoustic energy (8). Depending upon the application in measuring respiratory airflow pressure (7), the piezoelectric film (34) can have a thickness of about 50 micrometers to about 150 micrometers, and in particular embodiments, about 100 micrometers to about 120 micrometers. A piezoelectric film (34) suitable for embodiments can be obtained from Kueha America, 420 Lexington Avenue, Suite 2510, New York, NY 10170-0161. The electrically conductive layer (35) can comprise an electrically conductive foil (35A) which conductively overlays one or both piezoelectric film faces (34A)(34B) of the piezoelectric film (34). In particular embodiments, the electrically conductive layer (35) can, but need not necessarily, comprise an adhesive coated copper foil tape (35B) having a thickness ranging from about 0.0005 inches to about 0.010 inches with electrically conductive adhesive thicknesses ranging from about 0.002 inches to about 0.005 inches; however this illustrative example is not intended to preclude embodiments such as electrically conductive aluminum foil, electrically conductive paint, electrically conductive adhesive, or the like. An electrically conductive layer (35) suitable for use in embodiment can copper foil tape PN: 3313 available from 3M Corporate, St. Paul, MN 55144-1000. The electrical insulator layer (36) overlaying the electrically conductive layer (35) can, as an illustrative example, be a polyimide film (36A) having thickness of between about 7 micrometers to about 125 micrometers available from DUPONT® under the trademark KAPTON®.

Again, with primary reference to FIG. 6A, the respiratory airflow acoustic energy sensor (2C) can generate respiratory airflow acoustic energy data (5) varying based on sensed change in the respiratory air acoustic energy (8). In particular embodiments, the respiratory airflow acoustic sensor (2C) can comprise a microphone adapted to sense respiratory airflow acoustic energy (8) of about −40 dbV/Pa to about −15 dbV/Pa. As an illustrative example, a suitable respiratory air acoustic energy sensor (2C) can comprise a PN: SPU0414HR5H-SB available from Knowles Electronics, LLC, Itasca, IL.

Again, with primary reference to FIG. 6A, embodiments of the respiratory airflow measurement apparatus (1) can further include a processor unit (11) including a processor (11A) communicatively coupled to a non-transitory computer readable media (11B) containing a respiration rate measurement program (12). The processor (11A) and non-transitory computer readable media (11B) can, but need not necessarily, be a microprocessor unit (11') in the form of an integrated circuit that contains all the functions of a central processing unit of a computer and accepts binary data as input, processes it according to instructions stored in the memory, and provides results as output. The microprocessor unit (11) can receive and process sensor data (3)(4)(5) whether as analog data converted to binary data by an analog to digital convertor (37), whether discretely disposed on the printed circuit board (33) or integral to each of the plurality of sensors (2)(2A)(2B)(2C).

Now, with primary reference to FIGS. 5 and 6A, the processor unit (11) can further execute the program (12) to, in part, time processing events in the measure of respiratory rate (14) including initiating start of the first-time interval (28) and collection of pre-recording data (38) from each of the plurality of sensors (2) to establish a pre-recording baseline (39) for later comparative sensor data (3)(4)(5) comparison and to initiate the second time interval (29) and data collection in each successive measurement window (31) as the sliding measurement window (30) incrementally moves along the processing timeline (26).

Figure 5:
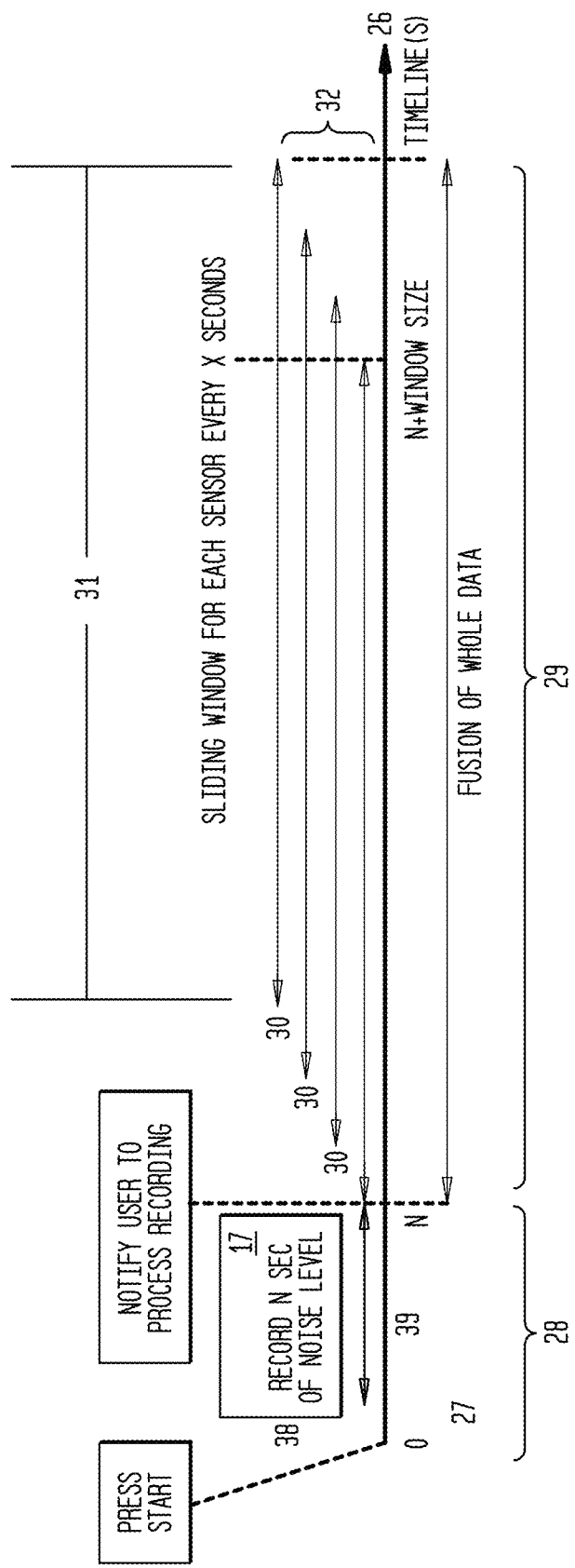
FIG. 5 is an illustration of a processing timeline in which sensor data within a sliding window is successively processed.
Figure 7A:
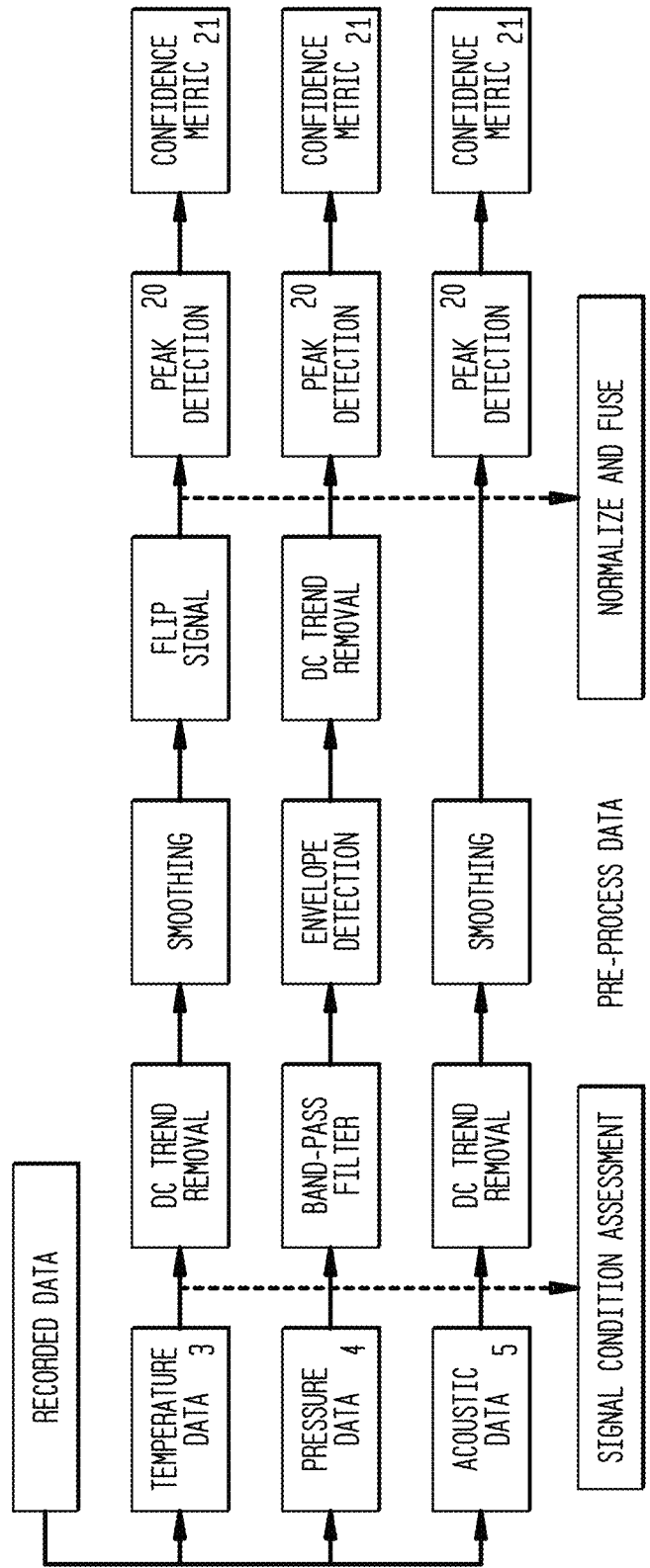
FIG. 7A is block flow diagram of pre-processing sensor data from embodiments of the respiration rate measurement apparatus shown in FIG. 6A.

Now, with primary reference to FIGS. 5, 6A and 7A, the processor (11) can further execute the program (12) to analyze the sensor data (3)(4)(5) from each sensor (2A)(2B)(2C) including comparing data collected in each of the overlapping measurement windows (32) generated by the sliding measurement window (31) to the pre-recorded baseline (39) for each of the plurality of sensors (2), and by comparison to one or more deviation thresholds (40), determines the suitability of the sensor data (3)(4) or (5) collected in each measurement window (31) for further processing (shown in FIG. 7A as "Signal Condition Assessment").

Again, with primary reference to FIGS. 5, 6A and 7A, the processor (11) can further execute the program (12) to pre-process the sensor data (3)(4)(5) to cancel noise, remove DC trend, and filter undesired frequency bands (as shown in FIG. 7A as "Pre-process Data").

Now referring primarily to FIGS. 2, 3, 5, 6A and 7A, the processor (11) can further execute the program (12) to discretely analyze respiration rate variability (20) in each of the respiratory airflow temperature data (3), the respiratory airflow pressure data (4), and the respiratory airflow acoustic energy data (5) collected in each overlapping measurement window (32) (as shown in the illustrative example of FIG. 3).

Now, with primary reference to FIGS. 2, 3, 6A and 7A, the processor (11) can further execute the program (12) to compute a confidence metric (21) by comparison of respiration rate variability (20) (or interval between successive breaths) to one or more variability rate thresholds (41).

Again, with primary reference to FIGS. 2, 3, 6A and 7A, the processor (11) can further execute the program (12) to utilize the confidence metrics (21) to generate correlation coefficients (23) which can be utilized in a covariance matrix (22) which can be correspondingly applied to the each of the respiratory airflow temperature data (3), the respiratory airflow acoustic energy data (4), and the respiratory airflow pressure data (5).

Figure 7B:
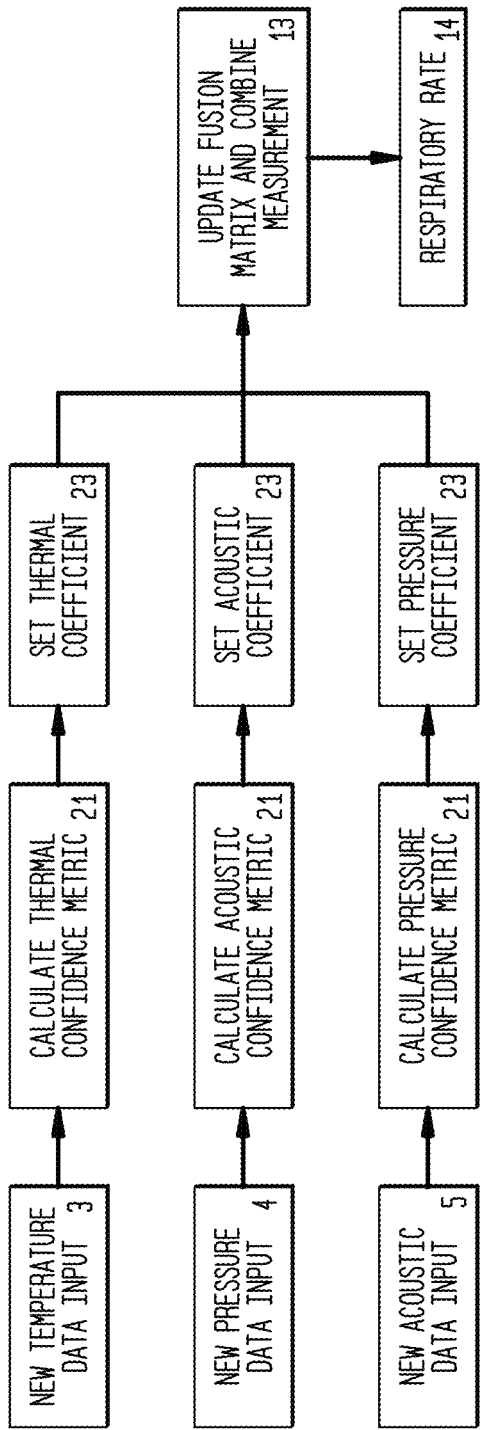
FIG. 7B is block flow diagram of processing sensor data from embodiments of the respiration rate measurement apparatus shown in FIG. 6A subsequent to pre-processing of data as shown in FIG. 7A and resulting a respiratory rate measurement.
Figure 8:
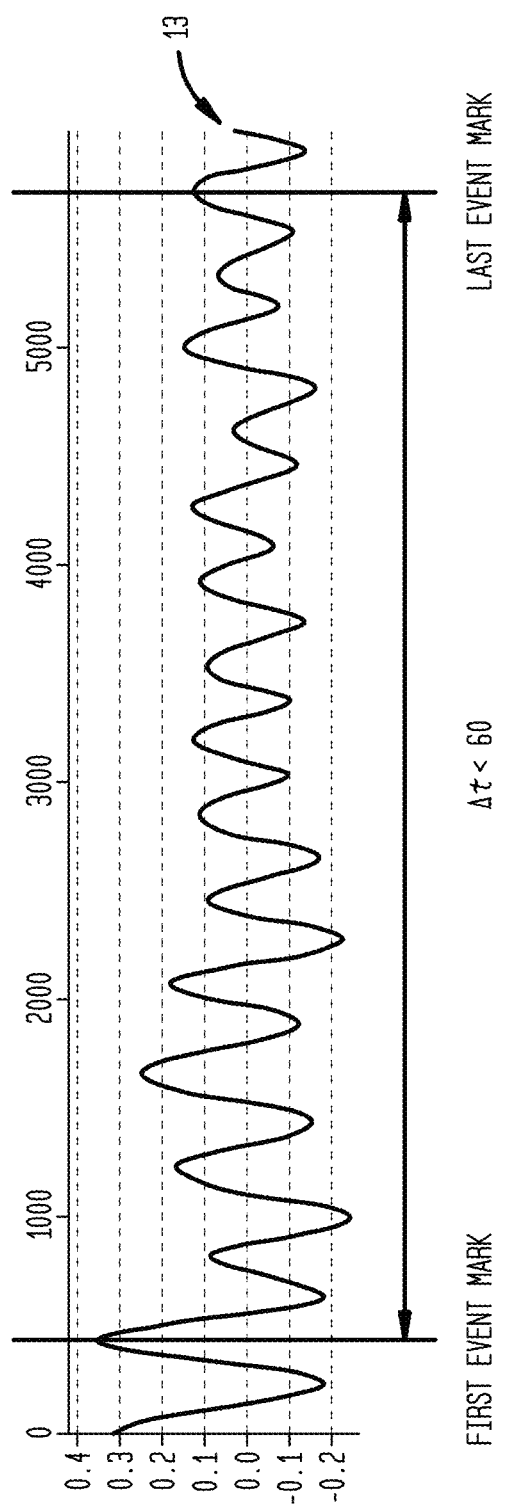
FIG. 8 is an illustration of method of calculating res sensor data to determine respiratory rate based on processed sensor data.

Now, with primary reference to FIGS. 2, 3, 6A, 7A and 7B, the processor (11) can further execute the program (12) to fuse the respiratory airflow temperature data (3), the respiratory airflow pressure data (4), and the respiratory airflow acoustic energy data (5) as a weighted average based on the applied correlation coefficients (23) to generate fusion respiratory rate data (13)(as shown in the example of FIG. 7B).

Again, with primary reference to FIGS. 2, 3, 6A, 7A and 7B and 8, the processor (11) can further execute the program (12) to calculate a respiratory rate (14) based on the fusion respiratory rate data (13). Where respiration rate (14) based on fusion respiratory rate data (13) can be calculated as:

$$\text{Respiratory Rate} = \frac{\Delta t \times 60}{\text{Number of events}}$$

Now, with primary reference to FIG. 6A, embodiments of the respiratory rate measurement apparatus (1) can further include a power management unit (42) which comprises a microcontroller which governs power functions of digital respiratory measurement apparatus (1). The power management unit (42) microcontroller includes firmware and software held in a memory element, a processor, input/output functions, timers to measure intervals of time, and analog to digital convertors to measure the voltages of the main battery or power source of the respiratory measurement apparatus (1).

Figure 9:
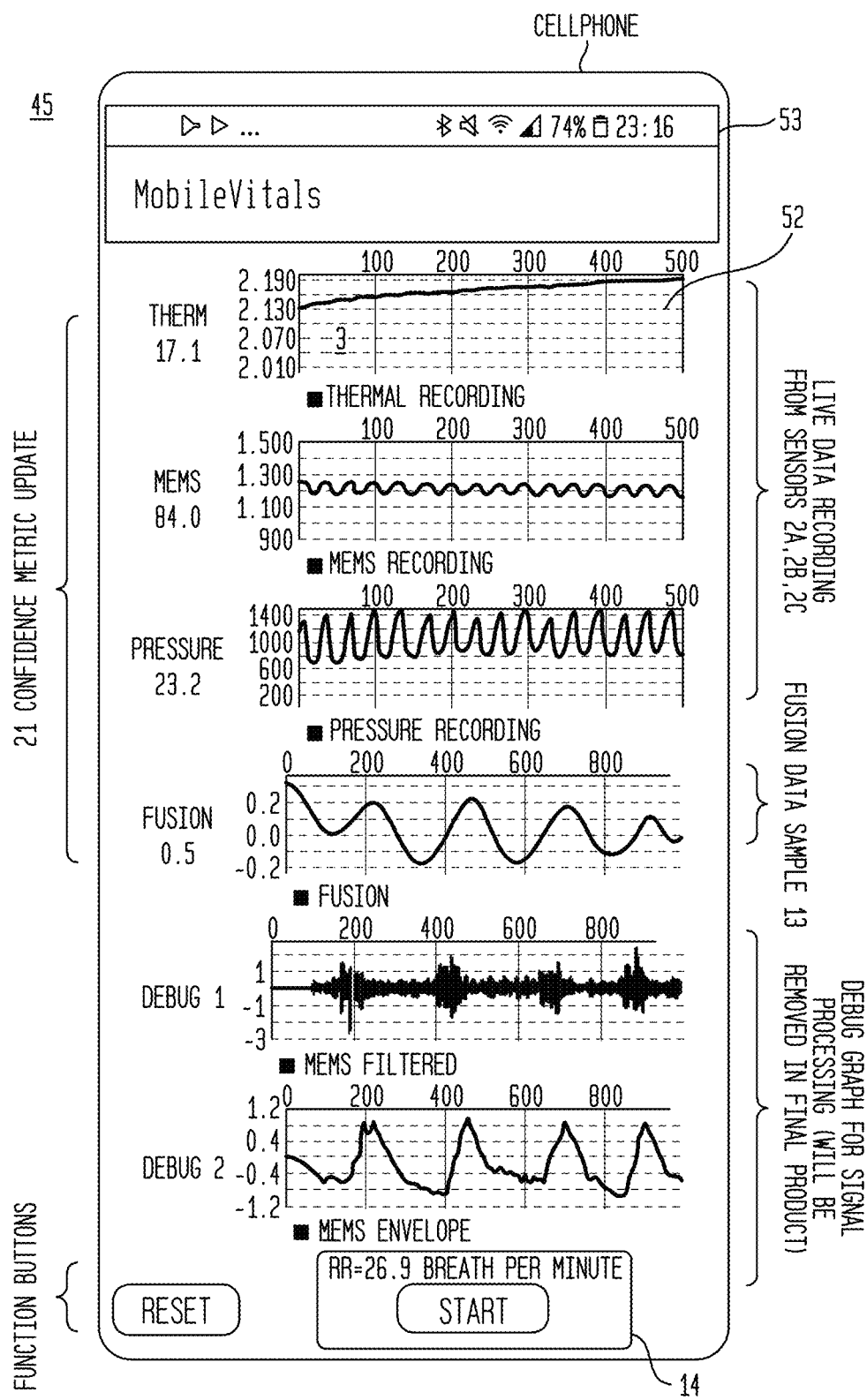
FIG. 9 is an illustration of an embodiment of a graphical user interface depicted on a display surface of a computer device depicting one or more of the respiratory airflow temperature data, the respiratory airflow acoustic energy data, the respiratory airflow pressure data, confidence metric, correlation coefficients, fusion respiratory rate data and the calculated respiratory rate.

Again, with primary reference to FIGS. 6A and 9, embodiments of the respiratory rate measurement apparatus (1) can, but need not necessarily, include an electronic data exchanger (43) operable by the processor unit (11) to transfer electronic data (44) including one or more of the respiratory airflow temperature data (3), respiratory airflow pressure data (4), and the respiratory airflow acoustic energy data (5), the correlation coefficients (23), the fusion respiratory rate data (13); and the respiratory rate (14) to a computing device (45) discrete from the respiratory rate measurement apparatus (1).

Figure 10:
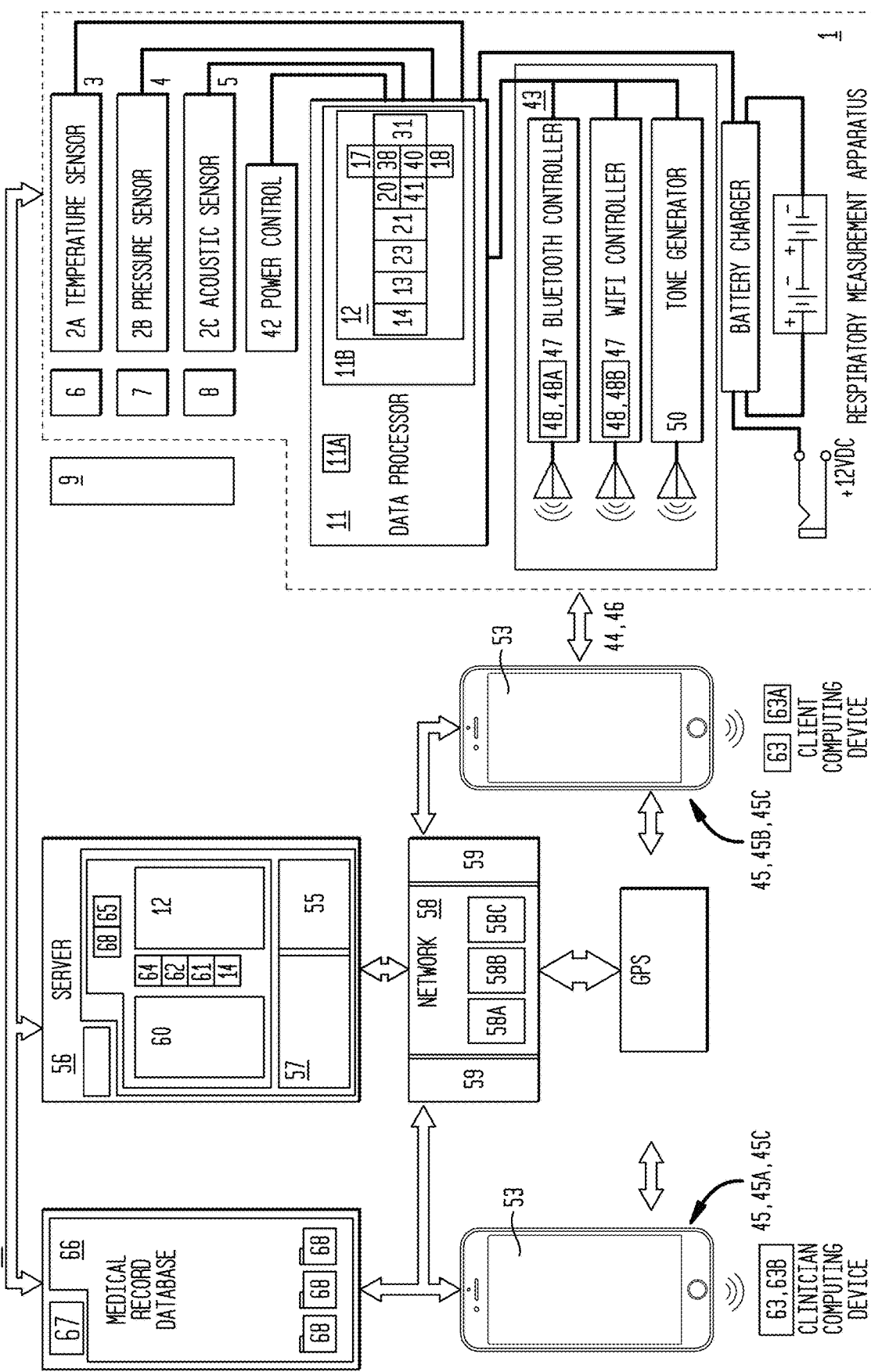
FIG. 10 is block flow diagram of a system including network elements, computer elements and software elements operable to support one or more computing devices to communicatively interconnect embodiments of the respiratory rate measurement apparatus.

Now, with primary reference to FIGS. 6A and 10, the electronic data exchanger (43) can transmit respiratory rate measurement apparatus pairing information (46) to the computing device (45). In particular embodiments, the respiratory rate measurement apparatus (1) can correspondingly include a radio frequency controller (47) which operates a radio frequency transmitter (48) to cause wireless connection or pairing of the respiratory rate measurement apparatus (1) with the computing device (45) over a short-range radio frequency band (49) to carry a signal over all or a part of the communication path between the respiratory rate measurement apparatus (1) and the computing device (45). The short-range frequency band (49) can include, as illustrative examples: BLUETOOTH® (49A) which operates at frequencies of about 2402 MHz to about 2480 MHz or about 2400 MHz to about 2483.5 MHz, or WI-FI® (49B) which operates at about 2.4 GHz or 5 GHz. In other particular embodiments, the respiratory rate measurement apparatus (1) can, but need not necessarily, include, a tone generator (50) which generates tones also referred to as an "audio beacon" that provides a signal over the communication path between the respiratory rate measurement apparatus (1) and the computing device (45).

Now, with primary reference to FIGS. 2, 6A, 7A, 7B, 9 and 10, the respiratory rate measurement apparatus (1) can further include a graphical user interface module (51) operable to depict a graphical user interface (52) on a display surface (53) of the computing device (45), the graphical user interface (52) depicting a representation of one or more of the respiratory airflow temperature data (3), the respiratory airflow acoustic energy data (4), the respiratory airflow pressure data (5), the confidence metrics, the correlation coefficients (23), the fusion respiratory rate data (13); and the calculated respiratory rate (14).

Embodiments of the respiratory rate measurement apparatus (1) can further include an exterior housing (69) configured to enclose the internal components of the apparatus (1). In particular embodiments, the exterior housing (69) can provide apertures through which respiratory airflow can be sensed by one or more of the temperature sensor (2A), the respiratory airflow pressure sensor (2B), and the respiratory airflow acoustic sensor (2C). In particular embodiments the exterior housing (69) can be configured to couple to a mobile computing device (63) or be configured as a mobile phone case.

Now referring primarily to FIG. 10, in particular embodiments, the respiratory rate measurement apparatus (1) (shown within broken line) and the computing device (45) can be disposed within a system (54) including network elements, computer elements and software elements operable to support one or a plurality of computing devices (45). In particular embodiments, the plurality of computing devices (45) can include a plurality of clinician computing devices (45A) correspondingly coordinated with a plurality of patient computing devices (45B). In particular embodiments, the plurality of computing devices (45) can include a plurality of subscriber computing devices (45C) each under a subscription plan (55). Each of the plurality of computing devices (45) makes requests of one or more servers (56) each having a server network interface (57) which operably couples the plurality of computing devices (45) by a public network (58), such as the Internet (58A), a cellular-based wireless network(s) (58B), or a local network (58C) (individually or collectively the "network" (58)).

The network (58) supports a plurality of communication resources (59) (along with other communication resources made available in the future) to afford as illustrative examples: recording, transmission, or reproduction of images (whether still or moving images), sound relating to acoustical, mechanical or electrical frequencies, electronic mail, instant messaging, text messaging (such as short message service) multimedia messaging (such as multimedia message service) attributable to the execution of self-contained programs or pieces of software designed to fulfill particular purposes (also referred to as "applications"), as illustrative examples: web applications, online applications, mobile applications, downloadable by a computing device (45).

The computing device (45) can include as illustrative examples: desktop computer devices, and mobile computer devices such as personal computers, slate computers, tablet or pad computers, cellular telephones, personal digital assistants, smartphones, programmable consumer electronics, or combinations thereof.

The network (58) can support the program (12) accessible by browser based on-line processing or downloadable by the computing devices (45) to enable off-line, wired or wireless connection with respiratory airflow measurement apparatus (1) operable as above described, to transfer electronic data (44) and calculate a respiratory rate (14). However, this is not intended to preclude embodiments in which the program (12) may be contained on and loaded to the computing device (45), the clinician computing device (45A), the patient computing device (45B), a subscriber computing device (45C), or the respiratory airflow measurement apparatus (1) from one or more of: a computer disk, universal serial bus flash drive, or other computer readable media.

In particular embodiments, the program (12) can, but need not necessarily, further include a respiratory airflow diagnostic module (60) operable to receive the calculated respiratory rate (14) from the respiratory airflow measurement apparatus (1) and compare the calculated respiratory rate (14) to a base-line average respiratory rate (61) of the user (63) of the respiratory airflow measurement apparatus (1), or to base-line average respiratory rates (62) based on age, geographic location, environmental conditions (such as temperature, pressure, particulate, pollutants, allergens) or other respiratory rate diagnostic values (64) as an indicator of potential respiratory dysfunction.

Illustrative examples of abnormal respiratory rates can result from one or combinations of: apnea, dyspnea, hyperpnea, tachypnea, hypopnea, bradypnea, orthopnea, platypnea, biot's respiration, cheyne-stokes respiration, kussmaul breathing, asthma or other condition whether solely due to physiological conditions or in response solely to environmental conditions or combinations thereof which place the respiratory rate (14) calculated by the respiratory airflow diagnostic apparatus (1) outside of the user base-line (61) or a base-line average respiratory rate (62) established for the user (63) of the respiratory airflow measurement apparatus (1).

In particular embodiments, the program (12) can be executed to communicate with the server (56) over the network (58) to coordinate operation of a patient computing device (63A) with operation of the respiratory airflow measurement apparatus (1) and a clinician computing device (63B). As an illustrative example, the program (12) can operate to transmit respiratory airflow measurement data (68) including a date-time stamp (65) to an electronic medical record (66) of the patient user (63A) associated with a user identification code (67). A clinician user (63B) can access the electronic medical record (66) associated with the identification code (67) of a patient user (63A) and retrieve the respiratory airflow measurement data (68) and diagnostic comparisons to the base-line (61) or (62) to provide remote diagnosis and treatment of patient users (63).

WORKING EXAMPLES

Working Example 1

Figure 11:
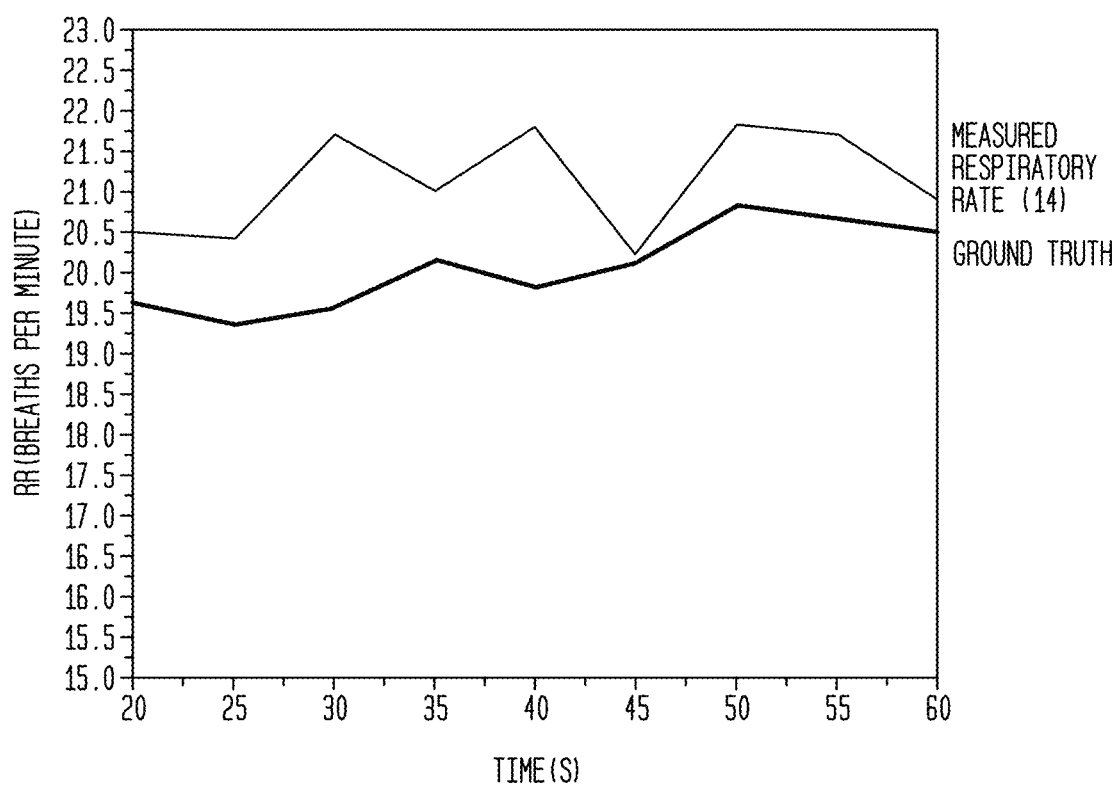
FIG. 11 is a line graph of respiratory rate calculated using an embodiment of the respiratory rate measurement apparatus compared to actual observed respiratory rate over time in a first working example.

Now referring primarily to FIG. 11, in a first working example an embodiment of the respiratory rate apparatus (1) was used to measure the respiratory rate (14) of a User 1. User 1 breathed (10) through the nostrils (15) having the respiratory rate apparatus (1) disposed in the respiratory airflow (9). User 1 was observed to breath at a moderate rate of about 19 breaths per minute ("BPM") (as shown by the graph line marked "Ground Truth"). The respiratory rate apparatus (1) was engaged with the respiratory airflow (9) as illustrated in FIG. 1A for about 60 seconds. The respiratory airflow temperature data (3), the respiratory airflow pressure data (4), and the respiratory airflow acoustic data (5) was acquired and processed by the respiratory rate measurement apparatus (1), as above described, to yield a respiratory rate (14)(as shown by the graph line marked "Respiratory Rate"). The "Ground Truth" having a standard deviation of +/− about 1 BPM. The respiratory rate measurement apparatus (1) yield a respiratory rate (14) having standard deviation of about +/−1 BPM.

Working Example 2

Figure 12:
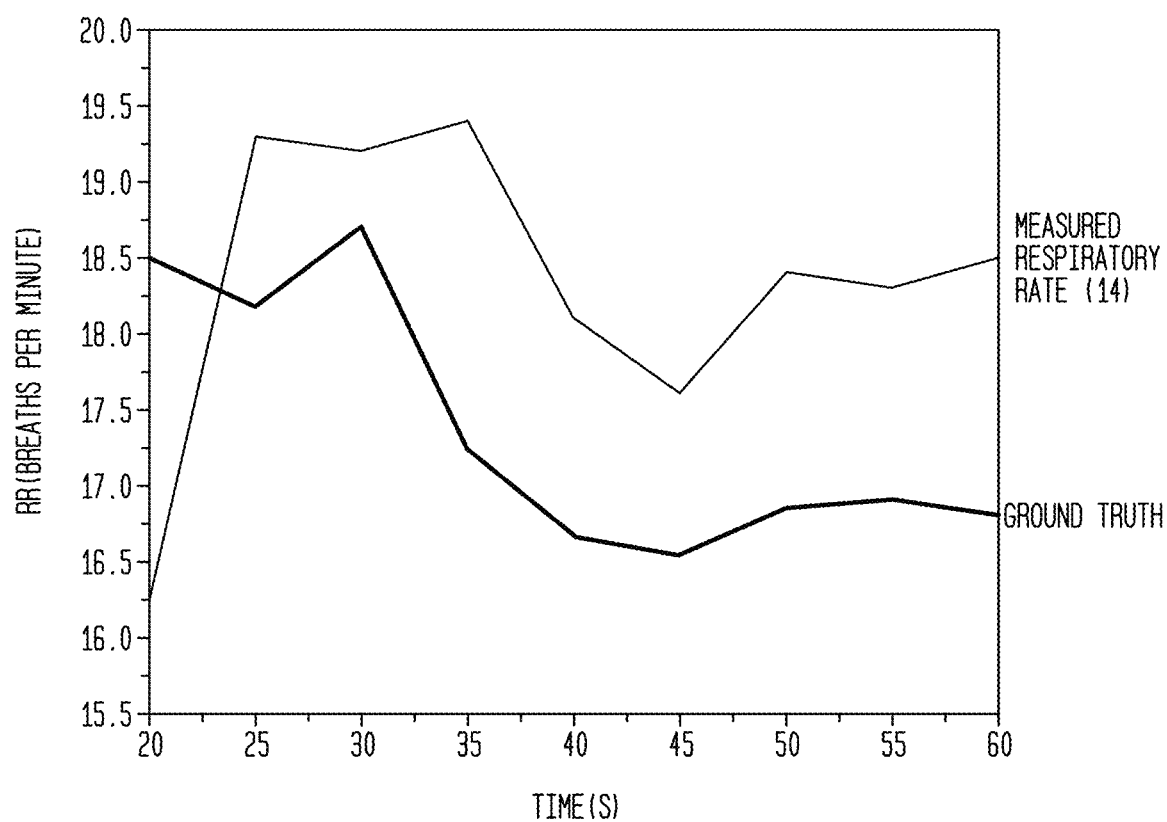
FIG. 12 is a line graph of respiratory rate calculated using an embodiment of the respiratory rate measurement apparatus compared to actual observed respiratory rate over time in a second working example.

Now referring primarily to FIG. 12, in a second working example an embodiment of the respiratory rate apparatus (1) was used to measure the respiratory rate (14) of a User 2. User 2 breathed (10) through the nostrils (15) having the respiratory rate apparatus (1) disposed in the respiratory airflow (9). User 2 was observed to breath at a moderate rate of about 19 BPM (as shown by the graph line marked "Ground Truth"). The respiratory rate apparatus (1) was engaged with the respiratory airflow (9) as illustrated in FIG. 1A for about 60 seconds. The respiratory airflow temperature data (3), the respiratory airflow pressure data (4), and the respiratory airflow acoustic data (5) was acquired and processed by the respiratory rate measurement apparatus (1), as above described, to yield a respiratory rate (14) (as shown by the graph line marked "Respiratory Rate"). The "Ground Truth" having a standard deviation of +/− about +/−1 BPM. The respiratory rate measurement apparatus (1) yield a respiratory rate (14) having standard deviation of about +/−1 BPM.

Working Example 3

Figure 13:
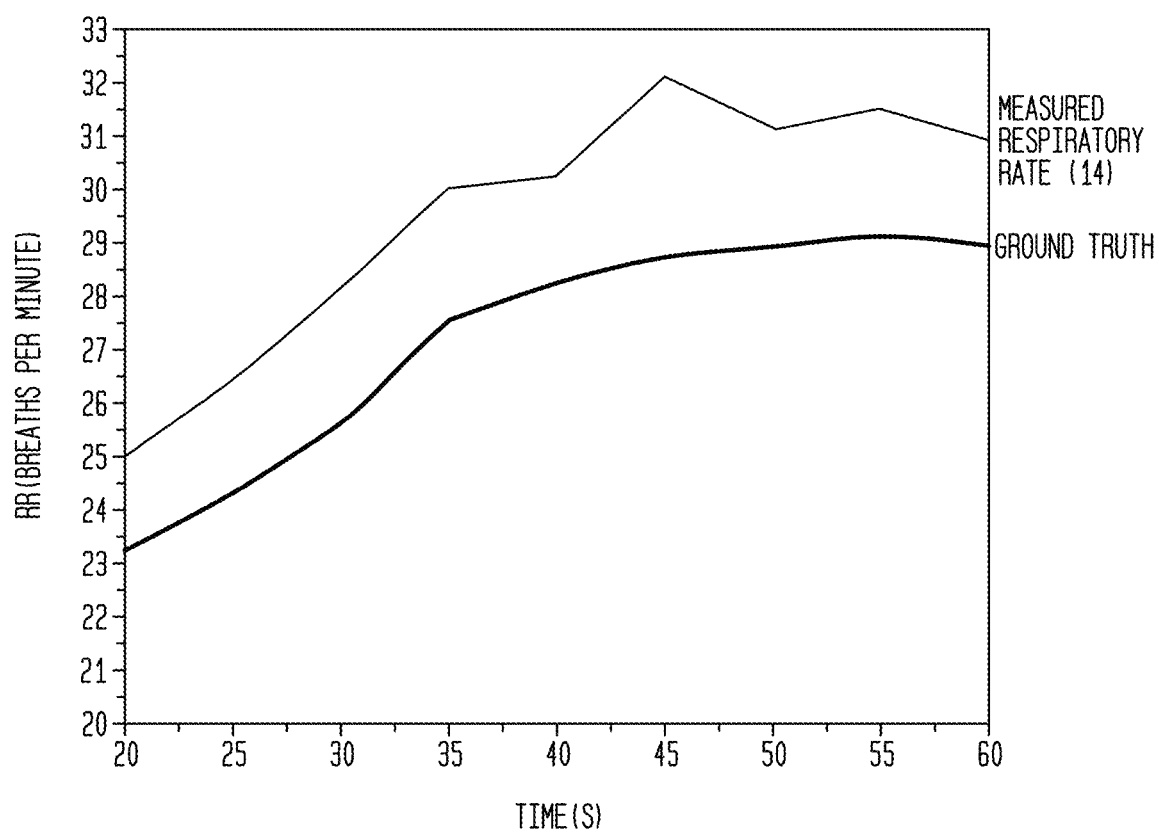
FIG. 13 is a line graph of respiratory rate calculated using an embodiment of the respiratory rate measurement apparatus compared to actual observed respiratory rate over time in a third working example.

Now referring primarily to FIG. 13, in a third working example an embodiment of the respiratory rate apparatus (1) was used to measure the respiratory rate (14) of a User 3. User 3 breathed (10) through the nostrils (15) having the respiratory rate apparatus (1) disposed in the respiratory airflow (9). User 3 was observed to breath at a fast rate of about 23 BPM to about 28 BPM (as shown by the graph line marked "Ground Truth"). The respiratory rate apparatus (1) was engaged with the respiratory airflow (9) as illustrated in FIG. 1A for about 60 seconds. The respiratory airflow temperature data (3), the respiratory airflow pressure data (4), and the respiratory airflow acoustic data (5) was acquired and processed by the respiratory rate measurement apparatus (1), as above described, to yield a respiratory rate (14)(as shown by the graph line marked "Respiratory Rate"). The "Ground Truth" having a standard deviation of +/− about +/−1 BPM. The respiratory rate measurement apparatus (1) yield a respiratory rate (14) having standard deviation of about +/−1 BPM.

Working Example 4

Figure 14:
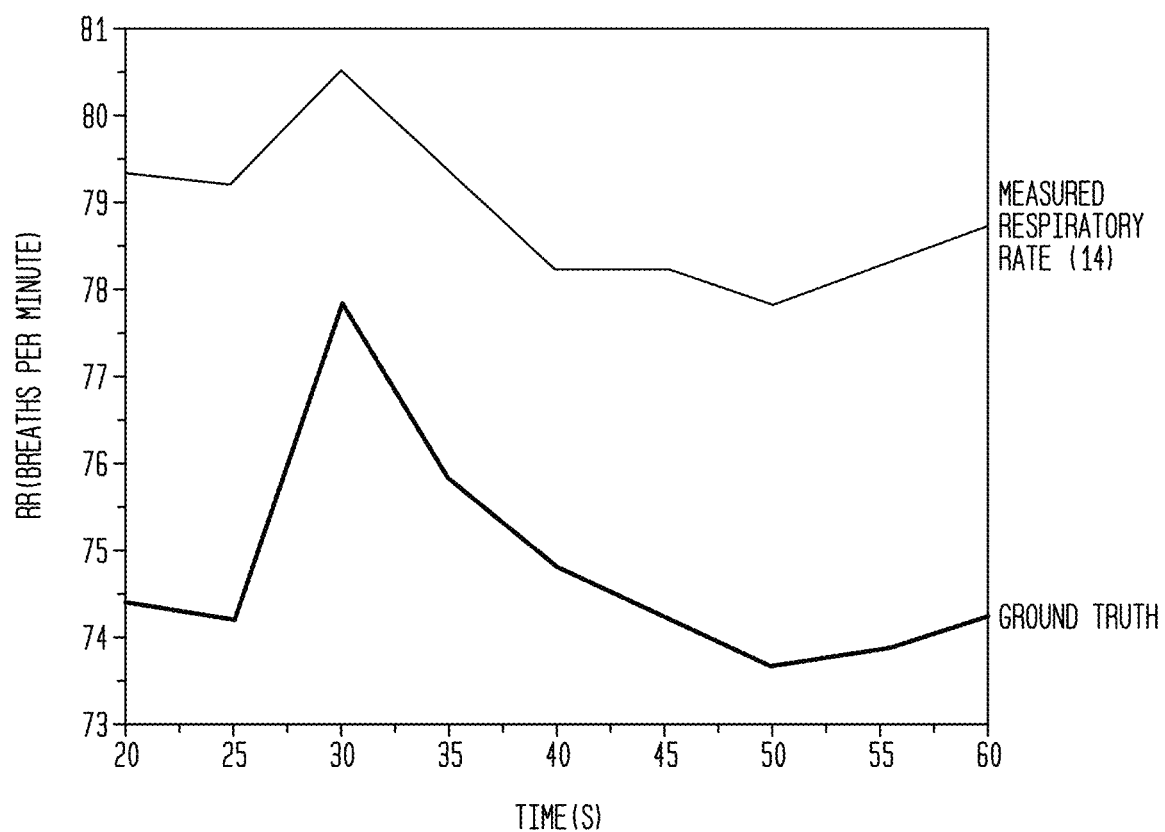
FIG. 14 is a line graph of respiratory rate calculated using an embodiment of the respiratory rate measurement apparatus compared to actual observed respiratory rate over time in a fourth working example.

Now referring primarily to FIG. 14, in a third working example an embodiment of the respiratory rate apparatus (1) was used to measure the respiratory rate (14) of a User 4. User 4 breathed (10) through the nostrils (15) having the respiratory rate apparatus (1) disposed in the respiratory airflow (9). User 4 was observed to breath at a very fast rate of about 75 BPM to about 81 BPM (as shown by the graph line marked "Ground Truth"). The respiratory rate apparatus (1) was engaged with the respiratory airflow (9) as illustrated in FIG. 1A for about 60 seconds. The respiratory airflow temperature data (3), the respiratory airflow pressure data (4), and the respiratory airflow acoustic data (5) was acquired and processed by the respiratory rate measurement apparatus (1), as above described, to yield a respiratory rate (14)(as shown by the graph line marked "Respiratory Rate"). The "Ground Truth" having a standard deviation of about +/−1 BPM to about +/−4 BPM. The respiratory rate measurement apparatus (1) yield a respiratory rate (14) having standard deviation of about +/−1 BPM to about +/−4 BPM.

As can be easily understood from the foregoing, the basic concepts of the present invention may be embodied in a variety of ways. The invention involves numerous and varied embodiments of a respiratory measurement apparatus and methods of making and using such respiratory measurement apparatus including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "sensor" should be understood to encompass disclosure of the act of "sensing"—whether explicitly discussed or not—and, conversely, were there effectively disclosure of the act of "sensing", such a disclosure should be understood to encompass disclosure of a "sensor" and even a "means for sensing." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the mountable carriers herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A respiratory rate measurement apparatus, comprising:
  a respiratory air temperature sensor adapted to sense respiratory air temperature in a respiratory air flow, said respiratory air temperature sensor generating respiratory air temperature data varying based on sensed change in said respiratory air temperature;
  a respiratory air acoustic sensor adapted to sense respiratory air acoustic energy in said respiratory air flow, said respiratory air acoustic sensor generating respiratory air acoustic energy data varying based on sensed change in said respiratory air acoustic energy;
  a respiratory air pressure sensor adapted to sense respiratory air pressure in said respiratory air flow, said respiratory air pressure sensor generating respiratory air pressure data varying based on sensed change in respiratory air pressure;
  a processor unit operable to:
    determine whether each of said respiratory air temperature data, said respiratory air acoustic energy data, and said respiratory air pressure data has a signal condition level sufficient to pre-process;

pre-process each of said respiratory air temperature data, said respiratory air acoustic energy data, and said respiratory air pressure data to remove noise and dielectric data trends;

discretely analyze variability in intervals between successive breaths in each of said respiratory air temperature data, said respiratory air acoustic energy data, and said respiratory air pressure data collected over a time period;

determine confidence metrics based on said variability in said intervals between successive breaths in each of said respiratory air temperature data, said respiratory air acoustic energy data, and said respiratory air pressure data by comparison to a pre-selected variable rate threshold;

determine correlation coefficients based on said confidence metrics of each of said respiratory air temperature data, said respiratory air acoustic energy data, and said respiratory air pressure data collected over said time period;

measure covariance of said correlation coefficients of each of said respiratory airflow temperature data, said respiratory airflow pressure data and said respiratory airflow acoustic energy data;

generate fusion respiratory rate data of said respiratory air temperature data, said respiratory air acoustic energy data, and said respiratory air pressure data collected over said time as a weighted average based on measured covariance between said correlation coefficients; and calculate a respiratory rate based on said fusion respiratory rate data.

2. The apparatus of claim 1, wherein said respiratory air temperature sensor, said respiratory air acoustic sensor, and said respiratory air pressure sensor have a fixed spatial relationship to concurrently sense said respiratory air flow.

3. The apparatus of claim 1, wherein said temperature sensor comprises a thermistor adapted to sense respiratory air temperature of 20° C. to 45° C.

4. The apparatus of claim 1, wherein said acoustic sensor comprises a microphone adapted to sense respiratory acoustic energy of 40 dbV/Pa to 15 dbV/Pa.

5. The apparatus of claim 1, wherein said pressure sensor comprises a piezoelectric film overlaid by a conductive layer.

6. The apparatus of claim 5, wherein said piezoelectric film has a thickness of 20 micrometers to 200 micrometers.

7. The apparatus of claim 6, wherein said pressure sensor further comprises an electrical insulator layer overlaying said conductive layer.

8. The apparatus of claim 1, further comprising an electronic data exchanger operable by said processor unit to transfer electronic data including one or more of said respiratory air temperature data, said respiratory air acoustic energy data, and said respiratory air pressure data, said correlation coefficients, said fusion respiratory rate data; and said respiratory rate to a computing device discrete from said respiratory rate measurement apparatus.

9. The apparatus of claim 8, further comprising a radio frequency transmitter operable to wirelessly transmit said electronic data to a radio frequency receiver of said computing device.

10. The apparatus of claim 9, wherein said radio frequency transmitter and said radio frequency operate at frequencies of about 2402 MHz to about 2480 MHz or 2400 MHz to 2483.5 MHz.

11. The apparatus of claim 9, wherein said computing device comprises a mobile computing device.

12. The apparatus of claim 11, further comprising a graphical user interface module operable to generate a graphical user interface on a display surface of said computing device, said graphical user interface depicting a representation of one or more of said respiratory air temperature data, said respiratory air acoustic energy data, and said respiratory air pressure data, said correlation coefficients, said fusion respiratory rate data; and said respiratory rate.

13. The apparatus of claim 1, wherein said processor unit is further operable to:

generate a sliding measurement window including a plurality of overlapping measurement windows over said period of time; and collect said respiratory air temperature data, said respiratory air acoustic energy data, and said respiratory air pressure data in each of said plurality of overlapping measurement windows over said time period.

14. The apparatus of claim 13, wherein said processor unit is further operable to:

compare said respiratory air temperature data, said respiratory air acoustic energy data, and said respiratory air pressure data collected in each of said plurality of overlapping measurement windows to a baseline for each of said respiratory air temperature data, said respiratory air acoustic energy data, and said respiratory air pressure data; and assess deviation of said respiratory air temperature data, said respiratory air acoustic energy data, and said respiratory air pressure data collected in each of said plurality of overlapping measurement windows to said baseline for each of said respiratory air temperature data, said respiratory air acoustic energy data, and said respiratory air pressure data;

compare said deviation to one or more deviation thresholds; and determine, based on comparison of said deviation to said one or more deviation thresholds, suitability of processing said respiratory air temperature data, said respiratory air acoustic energy data, and said respiratory air pressure data collected in each of said plurality of overlapping measurement windows.

15. The apparatus of claim 13, wherein said processor unit is further operable to:

determine additional confidence metrics based on said respiratory air temperature data, said respiratory air acoustic energy data, and said respiratory air pressure data collected in each of said plurality of overlapping measurement windows; and update said fusion data based on the additional confidence metrics.

* * * * *